(12) United States Patent
Pugh et al.

(10) Patent No.: US 9,801,758 B2
(45) Date of Patent: Oct. 31, 2017

(54) METHOD AND OPHTHALMIC DEVICE FOR GALVANIC HEALING OF AN EYE

(71) Applicant: Johnson & Johnson Vision Care, Inc., Jacksonville, FL (US)

(72) Inventors: Randall Pugh, Jacksonville, FL (US); Annabelle Gallois-Bernos, Jacksonville, FL (US); Adam Toner, Jacksonville, FL (US); Andres Arrubla, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 13/928,689

(22) Filed: Jun. 27, 2013

(65) Prior Publication Data
US 2014/0005514 A1    Jan. 2, 2014

Related U.S. Application Data

(60) Provisional application No. 61/665,964, filed on Jun. 29, 2012.

(51) Int. Cl.
*A61F 9/00* (2006.01)
*A61B 3/10* (2006.01)
(Continued)

(52) U.S. Cl.
CPC .......... *A61F 9/0017* (2013.01); *A61N 1/0468* (2013.01); *A61N 1/36046* (2013.01); *G02B 1/043* (2013.01); *A61B 3/10* (2013.01); *A61N 1/0448* (2013.01); *A61N 1/205* (2013.01); *A61N 1/306* (2013.01); *A61N 1/325* (2013.01); *A61N 1/326* (2013.01)

(58) Field of Classification Search
CPC .. A61N 1/326; A61N 1/0543; A61N 1/36046; A61N 1/0448; A61N 1/0468; A61F 9/0017; G02B 1/043
USPC ........... 607/2, 3, 53, 141; 600/318, 356, 383
See application file for complete search history.

(56) References Cited

U.S. PATENT DOCUMENTS

| 4,895,154 A | 1/1990 | Bartelt et al. |
| 6,417,027 B1 | 7/2002 | Akram |
| (Continued) | | |

FOREIGN PATENT DOCUMENTS

| WO | WO 2004/019078 A2 | 3/2004 |
| WO | WO 2010036966 A1 | 4/2012 |

OTHER PUBLICATIONS

Report from the Intellectual Property Office of Singapore dated Apr. 7, 2014 for Application No. 201305629-6.
(Continued)

*Primary Examiner* — Christopher D Koharski
*Assistant Examiner* — Pamela M Bays

(57) ABSTRACT

An apparatus for controlled healing of ocular erosions is described. The apparatus comprising; an optical surface comprising an energizable controller capable of being programmed to transmit energy from an energy source onto/into an ocular surface, through the use of a current generator in electrical connection with energy emitting contacts capable of transmitting an electric field. The controller, current generator and energy emitting contacts are biocompatible or encapsulated by a conductive biocompatible layer to allow positioning of said apparatus in an ocular surface.

20 Claims, 7 Drawing Sheets

(51) Int. Cl.
    *A61N 1/04*    (2006.01)
    *A61N 1/36*    (2006.01)
    *G02B 1/04*    (2006.01)
    A61N 1/30      (2006.01)
    A61N 1/20      (2006.01)
    A61N 1/32      (2006.01)

(56) References Cited

U.S. PATENT DOCUMENTS

| | | |
|---|---|---|
| 6,479,890 B1 | 11/2002 | Trieu et al. |
| 2002/0035358 A1* | 3/2002 | Wang ................................ 606/5 |
| 2003/0040779 A1* | 2/2003 | Engmark et al. ............... 607/36 |
| 2004/0106965 A1* | 6/2004 | Chow .................. A61F 9/0017 607/54 |
| 2005/0010266 A1* | 1/2005 | Bogdanowicz ................. 607/53 |
| 2006/0167435 A1* | 7/2006 | Adamis et al. ............... 604/500 |
| 2006/0217783 A1* | 9/2006 | Harold ............................ 607/53 |
| 2007/0016074 A1* | 1/2007 | Abreu ........................... 600/475 |
| 2007/0093877 A1* | 4/2007 | Beecham et al. .............. 607/53 |
| 2007/0260171 A1 | 11/2007 | Higuchi et al. |
| 2009/0264966 A1 | 10/2009 | Blum et al. |
| 2010/0076553 A1 | 3/2010 | Pugh et al. |

OTHER PUBLICATIONS

International Search Report for PCTPCT/US2013/048213 dated Oct. 29, 2013.

* cited by examiner

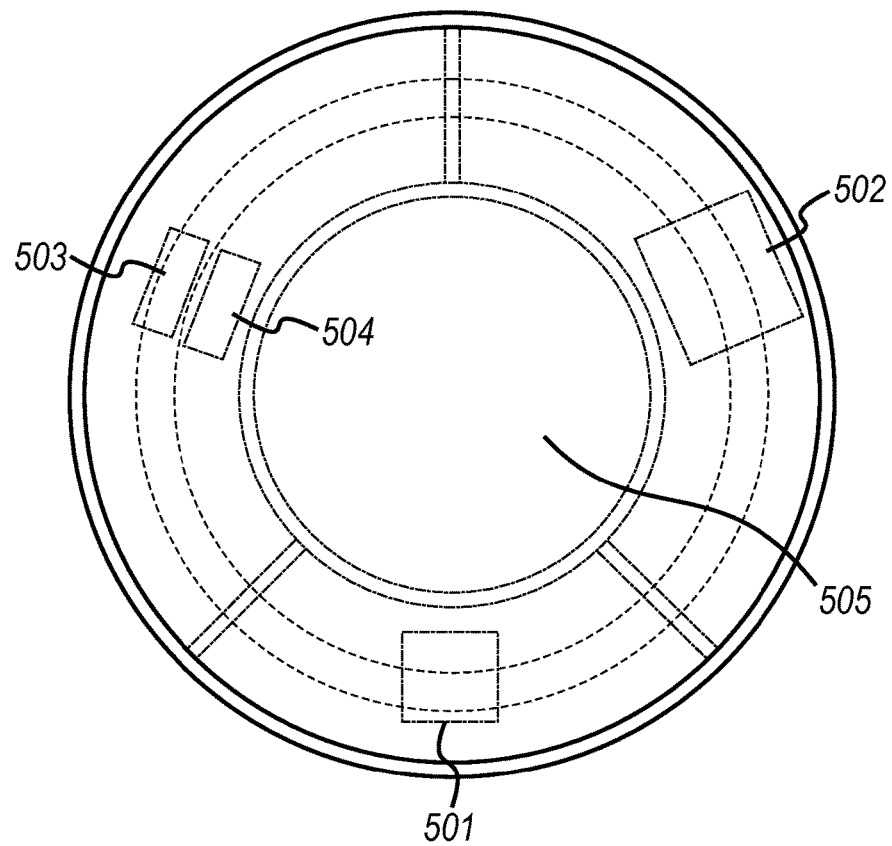
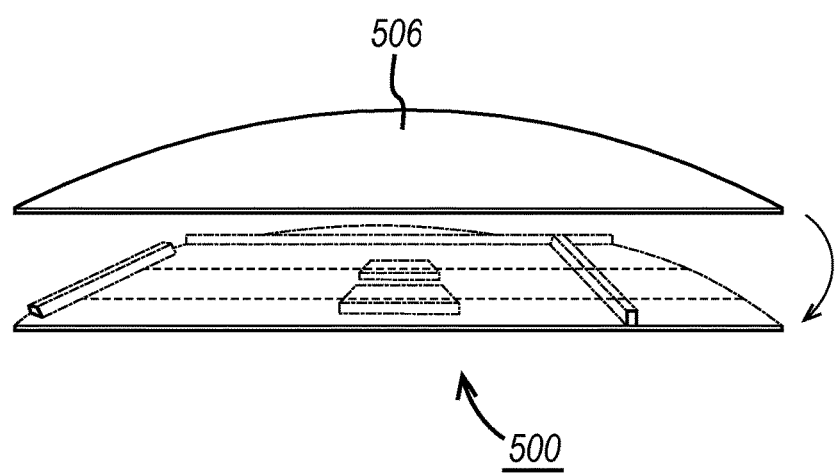
FIG. 5

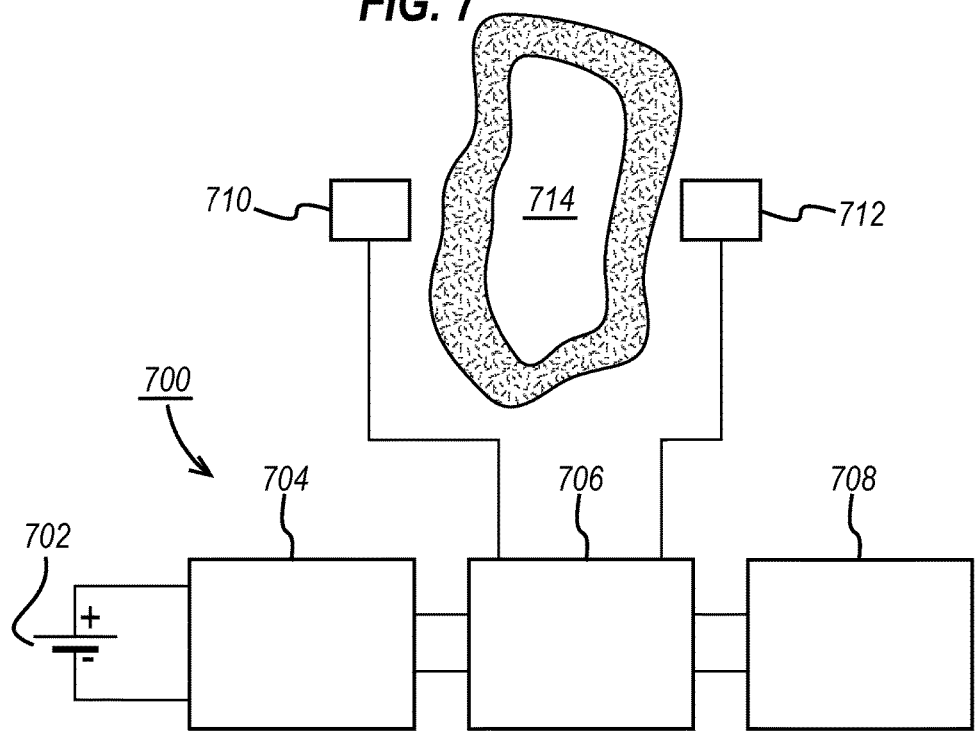
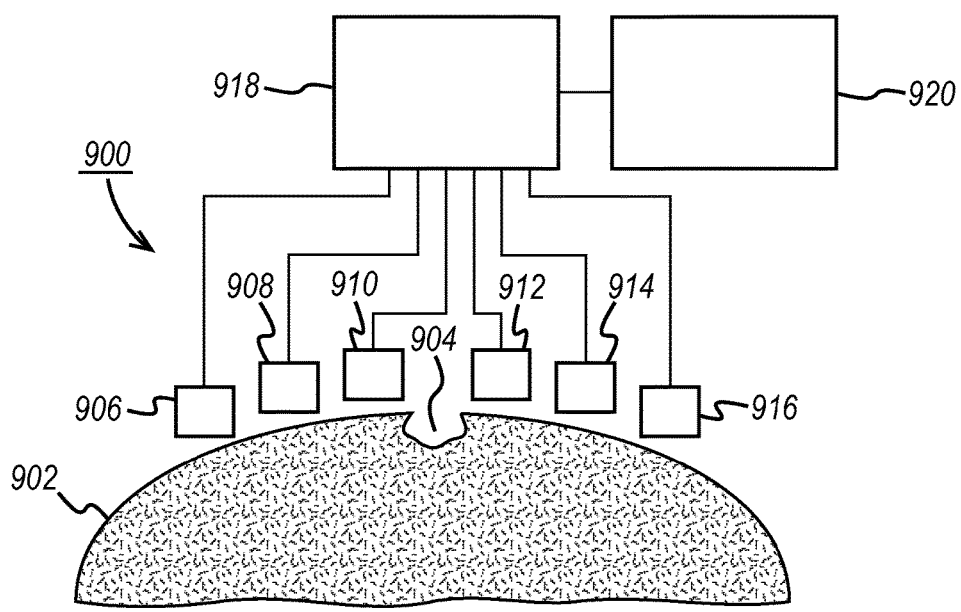

METHOD AND OPHTHALMIC DEVICE FOR GALVANIC HEALING OF AN EYE

CROSS-REFERENCE TO RELATED APPLICATION

This application claims the benefit of U.S. Provisional Application No. 61/665,964 filed Jun. 29, 2012.

FIELD OF USE

The invention relates to an energized ophthalmic device and methods of using said device. More specifically, the invention relates to an ophthalmic device used to optimize healing of an eye through the emission and control of an electric charge.

BACKGROUND

Traditionally, an ophthalmic device, such as a contact lens and an intraocular lens include one or more biocompatible device(s) with corrective, cosmetic, or therapeutic functionality. A contact lens, for example, may provide one or more of: vision correcting functionality; cosmetic enhancement; and therapeutic effects. Each function provided by a physical characteristic of the lens. For example, a design incorporating a refractive quality into a lens can provide a vision corrective function, a pigment incorporated into the lens can provide a cosmetic enhancement, and an active agent incorporated into a lens can provide a therapeutic functionality.

More recently, it has been theorized that active components may be incorporated into a contact lens for a variety of applications. In other applications filed concurrently by the same inventive entity of the present invention, the inventor teaches methods and apparatus for the fabrication of energized ophthalmic lenses.

Furthermore, it is known in the medical field that many physiological phenomena depend on endogenous supply of electricity or a bioelectric current, such as is the case during wound healing. Wounds generate endogenous electric currents. Vital cells that help wound healing respond to the generated endogenous electric currents, and more importantly, to applied electric signals. More recently, it has been found by various research groups that changes in wound currents are correlated directly with the rate of wound healing in vivo and thus, pharmacologically enhancing or decreasing wound healing may be proportional to the induced electric currents respectively.

Particularly to the eye, corneal erosions may be the source of tremendous pain to a subject, notably those experiencing recurrent erosions on their ocular surface. Erosions on an ocular surface can be the result of a variety of things, for example by a medical condition present in the patient's eye or induced in the process of medical treatment of the patient's eye.

Because the cornea is the tissue of the body that is most richly innervated by sensory nerves, the damage to the epithelium and the exposure of these nerve endings are associated with tremendous pain to the subject and may cause neurogenic inflammation until the epithelium can be sufficiently healed.

In such situations, it would be desirable to promote prompt healing of the ocular surface and notably mitigate inflammation-induced damage to the ocular surface and/or shorten the discomfort associated with the wounded eye. Such discomfort may cause eye rubbing and excessive blinking by the individual causing increased irritation and further inflaming the epithelium. In addition, ocular infections are associated with much risk of vision loss and thus may require fast and effective delivery of an anti-infectious agent to the eye.

As a result, it is desirable to have additional methods and apparatus conductive to wound healing promotion, healing control and infection treatment, to an extent that is suitable for an ophthalmic lens.

SUMMARY

Accordingly, aspects of the present invention are directed to an ophthalmic device and methods of using said device comprising electricity/batteries to form an electric field to influence or mediate directional migration of epithelial cells to thereby promote wound closure or healing of a wound. The ophthalmic device may be, for example, a hydrogel ophthalmic lens embedded with components able to generate a current or impart electrical conductivity when topically applied onto a damaged ocular surface (e.g. corneal erosions).

Using an ophthalmic device comprising active biocompatible components such as a battery and a microcontroller, the ophthalmic device can provide control of a current's intensity, modality, and direction. For example, a current and/or active drug that increases the conductivity of the naturally wound generated current can be directed towards the wound in order to promote wound closure. In other examples, it may also be desirable to have a randomly generated steady or pulsating current modality or reverse the direction of the current to control the wound healing response of the ocular surface.

In addition to the electric components, the device may additionally comprise an embedded reservoir for an active drug to be delivered to the ocular surface. The controlled current may additionally be used to cause the delivery of the active drug to the eye. The active drug can be used to further promote wound healing or treat other conditions of the eye through enhancement of the delivery of the active drug, for example the active drug may consist of an anti-infectious and/or anti-inflammatory or analgesic agent designed to provide relief to the subject and help restore the integrity of the mucosal membrane of the ocular surface.

In such situations, the current generated by the device may additionally promote an efficient transport of the drug to the targeted tissue by controlled use of the current (i.e. active transport) for the drug to be functional/effective. For example, to relieve plain, inflammation, treat infections, etc.

In a first aspect there is provided a method of controlling the healing of a wound in an ocular surface, the method comprising; examining an eye; diagnosing erosions in an ocular surface of the eye; gathering eye physiology data; fitting an ophthalmic device capable of delivering a controlled electric current; programming said current emitted by the ophthalmic device to aid a natural emitted current of the erosions in the ocular surface; and wearing said ophthalmic device during the healing of the diagnosed erosions.

The method may comprise delivering an active agent upon contact of said ophthalmic device with the ocular surface and wherein the delivery of the active agent is enhanced through the use of said current.

The method may comprise monitoring naturally emitted electric currents by the diagnosed ocular erosions.

The method may comprise detecting a change in the naturally emitted electric currents from a predetermined threshold signaling an infection or an increase in irritation of said ocular surface.

The method may comprise delivering an active agent upon a signal of an infection or increase in irritation of said ocular surface.

The method may comprise delivering the active agent in pre-determined doses and frequencies to effectively treat the signaled condition.

The method may comprise delivering an additional electrical charge to aid in the reception of the active agent by the ocular surface.

The method may comprise delivering said emitted current in one direction.

The method may comprise delivering said emitted current as a direct current toggling polarity.

The method may comprise delivering said emitted current as an alternating current.

The method may comprise delivering said emitted current in predetermined waveforms.

The method may comprise delivering said emitted current in predetermined frequencies.

In a second aspect, there is provided an apparatus for controlled healing of ocular erosions, the apparatus comprising; an optical surface comprising an energizable controller capable of being programmed to transmit energy from an energy source onto/into an ocular surface, through the use of a generator in electrical connection with energy emitting contacts capable of transmitting an electric field; and wherein the controller, generator and energy emitting contacts are biocompatible or encapsulated by a conductive biocompatible layer to allow positioning of said apparatus in an ocular surface.

The generator may comprise a current generator.

The generator may comprise one of a controlled voltage source, controlled current source, or an AC generator.

The optical surface may have an optical power other than about 0.

The energy may be stored in a battery embedded in the apparatus.

The battery may be embedded using stacked integrated component device packaging technologies.

The energy of the energy source may be obtained wirelessly through an RF antenna in connection with said ophthalmic device.

The RF antenna may be in connection with a device in proximity with the ophthalmic device.

The energy source may be contained within a pair of glasses.

The energy source may be contained within a patch.

The apparatus may comprise a reservoir capable of containing an active drug to be delivered in a predetermined manner.

The apparatus may comprise one or more sensors capable of measuring changes in the naturally emitted electric field by the ocular erosions.

The apparatus may be capable of delivering an active drug upon the sensor's detection of a change in electric field threshold signaling an infection.

The reservoir may contain an active drug comprising an analgesic.

The reservoir may contain an active drug comprising an antiviral agent.

The reservoir may contain an active drug comprising an anti-infective agent.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 5 illustrates another exemplary energized ophthalmic Lens configuration.

FIG. 7 illustrates an electrical system that may be used for monitoring and improving the healing of a wound.

FIG. 9 illustrates a therapeutic system for detecting and improving the healing of wounds across a range of wound locations.

DETAILED DESCRIPTION

Figure 1:
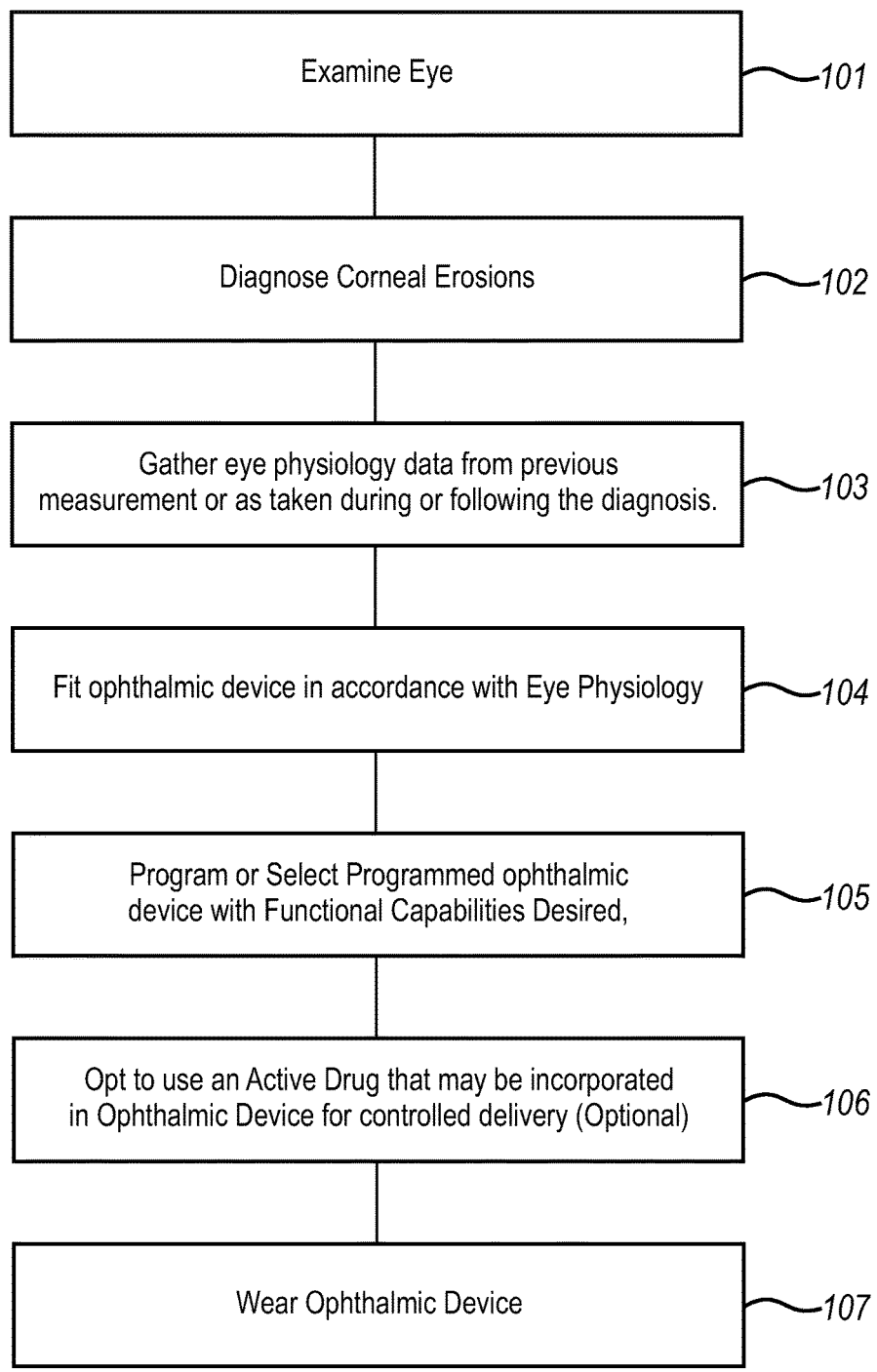
FIG. 1 illustrates exemplary method steps that can be implemented in accordance with an aspect of the present invention.

A method and an ophthalmic device that may be used to promote wound healing of an eye, galvanically, is described herein. In the following sections detailed descriptions of embodiments of the invention will be given. The description of method steps and both preferred and alternative embodiments are exemplary method steps and examples only, and it is understood that to those skilled in the art that variations, modifications, and alterations may be apparent. It is therefore to be understood that said exemplary method steps and embodiments do not limit the scope of the underlying invention.

GLOSSARY

In this description and claims directed to the presented invention, various terms may be used for which the following definitions will apply:

"Galvanic Healing" as used herein, refers to influencing the natural occurring endogenous electric current that results from a wound by pharmacologically and/or electrically controlling (e.g. enhancing or decreasing) one or both of, wound induced electric currents and direction of current to influence the healing rate and/or direction of healing. For example, using an energized ophthalmic device that is capable of generating a controlled electric field or delivering an active drug to manipulate the wounded cornea's transportation of Na+ and Cl− to significantly enhance or decrease healing.

"Energized" as used herein, refers to the state of being able to supply electrical current to a device component or to have electrical energy stored within.

"Energy" as used herein, refers to the capacity of a physical system to do work. Many uses described herein may relate to the said capacity being able to perform electrical actions in doing work.

"Energy Source" as used herein, refers to a device or layer which is capable of supplying Energy, or placing a logical or electrical device in an Energized state.

"Energy Harvesters" as used herein, refers to devices capable of extracting energy from the environment and converting it to electrical energy.

"Functionalized" as used herein, refers to making a layer or device able to perform a function including for example, energization, activation, or control.

"Lens" as used herein, refers to any ophthalmic device that resides in or on the eye. These devices may provide optical correction or may be cosmetic. For example, the term lens may refer to a contact lens, intraocular lens, overlay lens, ocular insert, optical insert or other similar device through which vision is corrected or modified, or through which eye physiology is cosmetically enhanced (e.g. iris color) without impeding vision. The preferred lenses are soft contact lenses are made from silicone elastomers, or hydrogels, which include but are not limited to silicone hydrogels, and fluorohydrogels.

"Lens Forming Surface" as used herein, refers to a surface that may be used to mold at least a portion of a lens. In some examples, any such surface may have an optical quality surface finish, which indicates that it is sufficiently smooth and formed so that a lens surface fashioned by the polymerization of a lens forming material in contact with the molding surface is optically acceptable. Further, the lens forming surface may have a geometry that is necessary to impart to the lens surface the desired optical characteristics, including without limitation, spherical, aspherical and cylinder power, wave front aberration correction, corneal topography correction and the like as well as any combinations thereof.

"Lithium Ion Cell" as used herein, refers to an electrochemical cell where Lithium ions move through the cell to generate electrical energy. This electrochemical cell, typically called a battery, may be reenergized, or recharged in its typical forms.

"Substrate Insert" as used herein, refers to a formable or rigid substrate capable of supporting an Energy Source within an ophthalmic lens. The substrate insert may also supports one or more components.

"Mold" as used herein, refers to a rigid or semi-rigid object that may be used to form lenses from uncured formulations. Some preferred molds include two mold parts forming a front curve mold part and a back curve mold part.

"Optical Zone" as used herein, refers to an area of an ophthalmic lens through which a wearer of the ophthalmic lens sees.

"Power" as used herein, refers to work done or energy transferred per unit of time.

"Rechargeable or Re-energizable" as used herein, refers to a capability of being restored to a state with higher capacity to do work. Many uses described herein may relate to the capability of being restored with the ability to flow electrical current at a certain rate for a certain, reestablished time period.

"Reenergize or Recharge" as used herein, refers to the restoration of energy to a state with higher capacity to do work. Many uses described herein may relate to restoring a device to the capability to flow electrical current at a certain rate for a certain, reestablished, time period.

"Stacked" as used herein, refers to the placing at least two component layers in proximity to each other such that at least a portion of one surface of one of the layers contacts a first surface of a second layer. A film, whether for adhesion or other functions, may reside between the two layers that are in contact with each other through said film.

"Stacked Integrated Component Devices" as used herein and sometimes referred to as "SIC-Devices", refers to the product of packaging technologies that can assemble thin layers of substrates, which may contain electrical and electromechanical devices, into operative integrated devices by means of stacking at least a portion of each layer upon each other. The layers may comprise component devices of various types, materials, shapes, and sizes. Furthermore, the layers may be made of various device production technologies to fit and assume various contours as it may be desired.

Methods and apparatus for galvanic healing of an eye are described. In the following sections, a method of using a lens to galvanically heal an eye is provided. Additionally, as described in referenced applications and further explained herein, exemplary embodiments that may be implemented for the present invention are described accordingly. For example, Stacked Integrated Component Device(s) may be incorporated in a lens for energization and to function in accordance with an aspect of the present invention.

Method

Eyes are protected by a cornea. The cornea is covered by a transparent stratified epithelium layer that not only can protect the eye from physical and chemical agents but also refracts light onto the lens and retina for vision. In order to perform these functions properly, the cornea must be able to maintain its integrity by cell proliferation and repair of any damage due to corneal erosions (i.e. wounds). Additionally, these corneal erosions may be the source of tremendous pain because the cornea is the tissue of the body that is most richly innervated by sensory nerves. The damage to the epithelium and the exposure of these nerve endings are associated with tremendous pain to the subject and may cause neurogenic inflammation until the epithelium may be sufficiently healed. In some circumstances also involving corneal erosions, ocular infections may also result. Ocular infections are associated with much risk of vision loss.

Said corneal wounds or erosions may be the result of a variety of things, for example from a medical condition present in the patient's eye or induced by an ophthalmologist in a process that is required for a certain medical treatment of the patient's eye. As a result, the method below may be used to control and enhance or decrease wound healing in predetermined ocular surfaces, such as for example the cornea.

Referring now to FIG. 1, exemplary method steps that may be implemented in accordance with an aspect of the present invention are illustrated in a flowchart. At 101, an eye is examined. The eye may be examined for by an eye care practitioner. For example, after one of many performed surgeries or when a subject visits the practitioner due to discomfort or to treat a corneal injury from physical impact of an object, etc.

At 102, the eye practitioner may diagnose one or more corneal erosions. Following examination, or during examination, or from a previously conducted eye examination, eye physiology data may be gathered at 103. At 104, an ophthalmic device is selected to fit in accordance with the gathered eye physiology. The device selected which may either be capable of being programmed in some applications where it may be needed or in some it may be selected from a standard set of pre-programmed lenses capable of having the functional capabilities desired by the practitioner in view of the diagnosis 105.

At 106, the practitioner may opt to incorporate or use an active drug that may be incorporated in the lens for controlled delivery. For example, this may include an antibiotic or anti-inflammatory drug that can be incorporated in parts of the lens and delivered at any frequency desired as it may be pre-determined or upon a received signal. The patient may then wear, at 107, the ophthalmic device for treatment for a predetermined amount of time and/or until a replacement is due as it may be determined by the eye practitioner.

Figure 2:
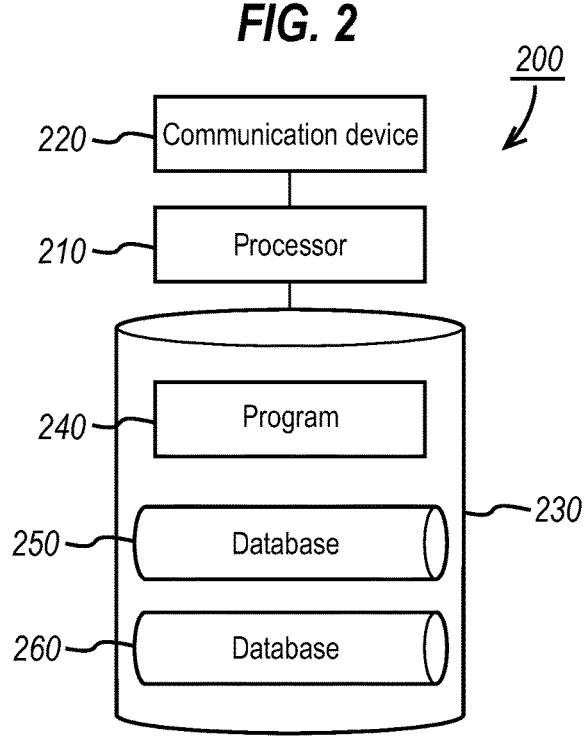
FIG. 2 illustrates a schematic diagram of an exemplary controller that may be used to implement an aspect of the present invention.

Referring now to FIG. 2, a controller 200 is illustrated that may be used. The controller 200 includes a processor 210, which may include one or more processor components coupled to a communication device 220. A controller 200 may be used to transmit energy from the energy source placed in the ophthalmic lens.

The controller may include one or more processors, coupled to a communication device configured to communicate energy via a communication channel. The communication device may be used to electronically control one or more of: an electrical field and an active drug component.

The communication device 220 may also be used to communicate, for example, with one or more controller apparatus or manufacturing equipment components.

The processor 210 may also be in communication with a storage device 230. The storage device 230 may comprise any appropriate information storage device, optical storage devices, and/or semiconductor memory devices such as Random Access Memory (RAM) devices and Read Only Memory (ROM) devices.

The storage device 230 may store a program 240 for controlling the processor 210. The processor 210 performs instructions of the program 240, and thereby operates in accordance with an aspect of the present invention. For example, the processor 210 may receive information descriptive of lens placement, effect of a delivered electric current, wound generated current, wound infection feedback and the like. The storage device 230 can also store ophthalmic related data in one or more databases 250, 260. The database 250,260 may include specific control logic for controlling energy to and from a lens.

Apparatus

Recent experiments have been performed to further study the effect and measure the current that results from wounds. Small natural occurring detected direct current (d.c.) electrical signals have been analyzed and measured to understand the relationship and function in particular wound environments. However, most of these experiments are performed in controlled environments and none have suggested or invented a practical apparatus or method that may be routinely used/followed and that can achieve the functions desired in particular environments in a controlled manner. To the contrary, the experiments use large devices, vibrating probes that must be cautiously used, and harmful reagents to humans.

In the referenced figures and their respective descriptions in the following section, the inventor describes the apparatus of this invention which may be capable of Functioning to promote controlled healing of one or more ocular surfaces, such as the epithelium layer in the cornea, in a biocompatible manner. More specifically, a lens, that may be placed in contact with an eye to promote and control the healing of stratified layers of epithelium cells found therein.

Figure 3:
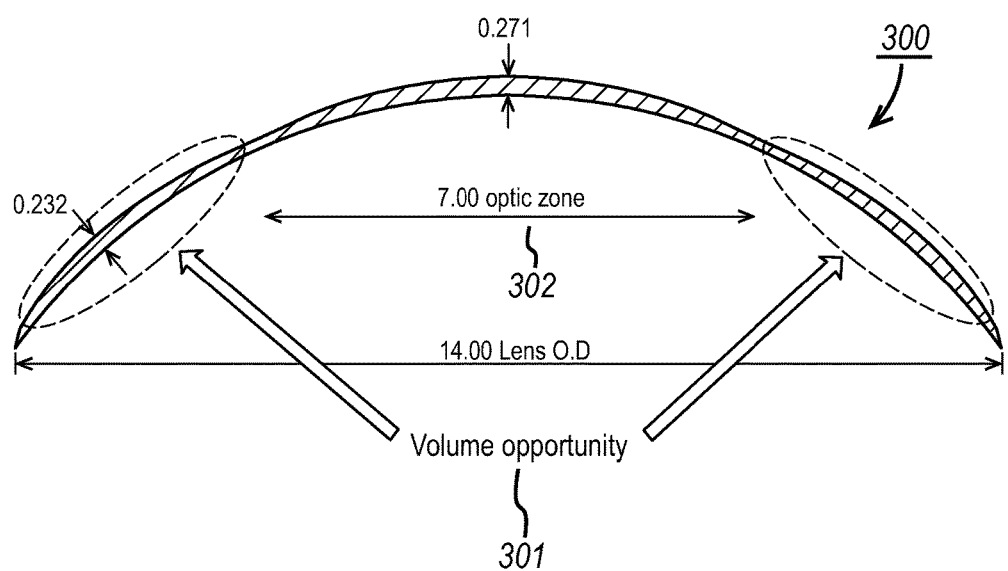
FIG. 3 illustrates a cross section of an exemplary ophthalmic Lens configuration.

Referring now to FIG. 3 a cross section of an exemplary ophthalmic lens configuration 300 is depicted. In the exemplary ophthalmic contact lens, the contact lens may be designed to have an optic zone 302 in the middle, surrounded by structures that may be designed for things such as: adjustment, positioning, or placement of the lens. Due to recent developments by the inventive entity of the present invention, it has been possible to safely place functional components in said surrounding structures 301 i.e. volume opportunity. Functional components may also be placed in the appropriate regions of contact lenses specifically designed for therapeutic functions, and these lenses may differ in design from common contact lenses used for spherical correction.

In order to use the volume surrounding the optical zone or limit the placement of functional parts that may significantly result in unwanted effects to the optical quality in the optic zone, one or a combination of SIC-Devices, or die on optic, or die on flex technologies with energization may be used. Said encapsulated energized devices may be capable of safely providing a controlled current and/or dispensing an active drug in a controlled manner.

Figure 4:
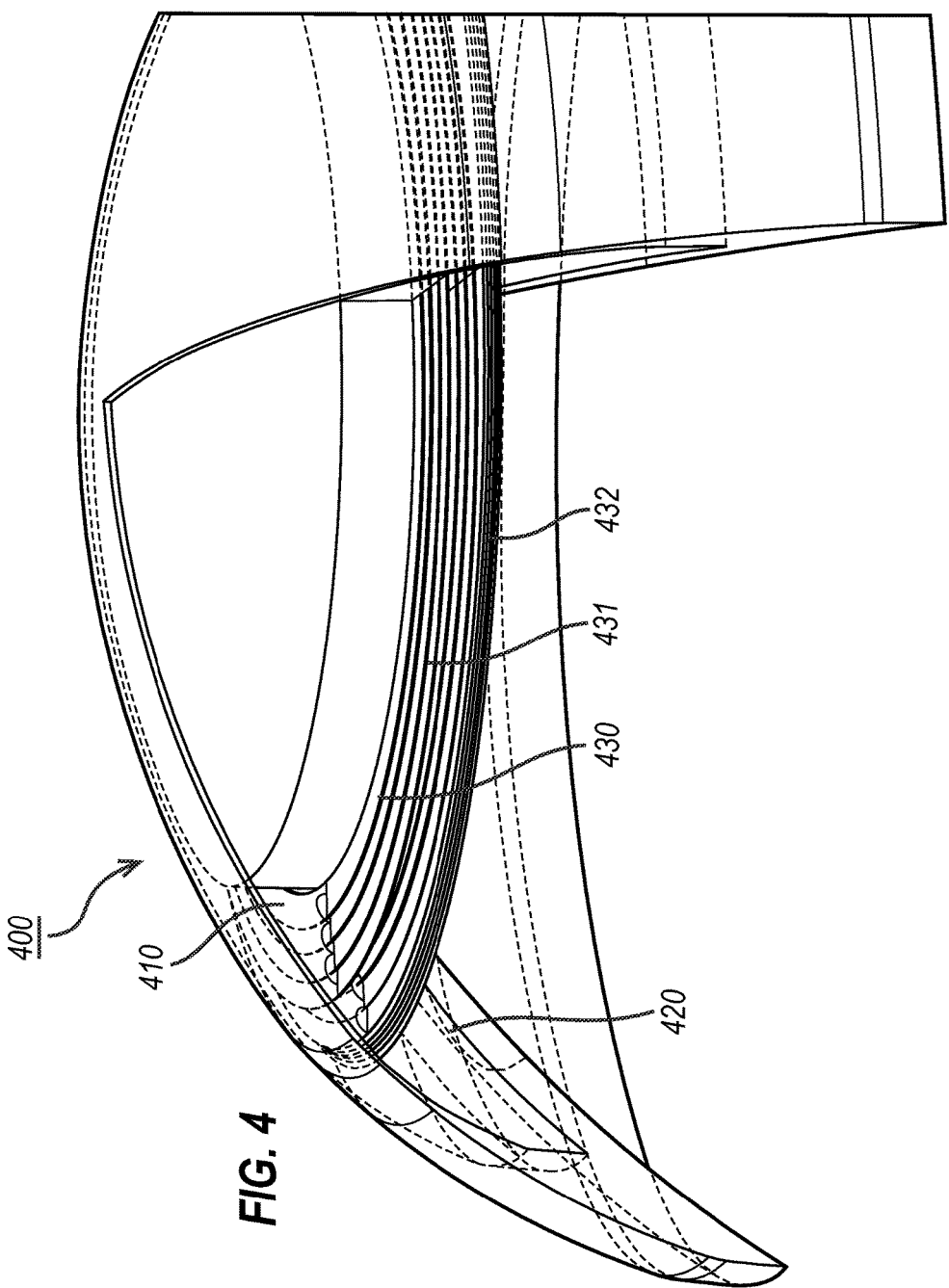
FIG. 4 illustrates a three dimensional representation of an insert formed of stacked functional layers which may be incorporated within an ophthalmic lens mold part.

Referring now to FIG. 4 an exemplary three-dimensional representation of SIC-Devices is illustrated in a fully formed ophthalmic lens 400 using a layer substrate insert of the type in item 410. The representation shows a partial cut out from the ophthalmic lens to realize the different layers present inside the device. Item 420 shows the body material in cross section of the encapsulating layers of the substrate insert. This item may surround the entire periphery of the ophthalmic lens as depicted. It may be clear to one skilled in the arts that the actual insert may comprise a full annular ring or other shapes that still may reside within the constraints of the size of a typical ophthalmic lens.

Items 430, 431 and 432 illustrate three of numerous layers that may be found in a substrate insert formed as a stack of functional layers. A single layer may include one or more of: active and passive components and portions with structural, electrical or physical properties conducive to a particular purpose.

A layer 430 may include an energization source, such as, for example, one or more of: a battery, a capacitor, and a receiver within the layer 430. Item 431 then, in a non-limiting exemplary sense may comprise microcircuitry in a layer that detects actuation signals for the ophthalmic lens.

A power regulation layer 432, may be included that is capable of receiving power from external sources, charges the battery layer 430 and/or may be capable of controlling the use of battery power from layer 430 when the lens is not in a charging environment. The power regulation may also control signals to an exemplary active lens, demonstrated as item 410 in the center annular cutout of the substrate insert.

An energized lens with an embedded substrate insert may include an energy source, such as an electrochemical cell or battery as the storage means for the energy and in some examples, encapsulation, and isolation of the materials comprising the energy source from an environment into which an ophthalmic lens is placed.

A substrate insert may also include a pattern of circuitry, components and energy Sources. Various examples may include the substrate insert locating the pattern of circuitry, components and energy sources around a periphery of an optic zone through which a wearer of a lens would see, while other examples may include a pattern of circuitry, components and energy sources which are small enough to not adversely affect the sight of a contact lens wearer and therefore the substrate insert may locate them within, or exterior to, an optical zone.

In general, a substrate insert may be embodied within an ophthalmic lens via automation which places an energy source a desired location relative to a mold part used to fashion the lens.

One or more layers of a functionalized stack of substrates may include a thin film electrical power source. The thin electrical power source may be viewed essentially as a battery on a substrate. A thin film battery (sometimes referred to as a TFB) may be structured on a suitable substrate, such as silicon, using known deposition processes to deposit materials in thin layers or films. The deposition process for one of these thin film layers may include, sputter deposition and may be used to deposit various materials. After a film is deposited, it may be processed before a next layer is deposited. A common process on a deposited film may include lithography or masking techniques that then allow etching or other material removing techniques to be performed thus allowing the film layer to have a physical shape in the two dimensions of the substrate surface.

The layers may be encapsulated with Parylene and Titanium or with epoxy and Glass layers. The layers may be encapsulated with Parylene, Titanium, epoxy, glass, or other layers. As with other layers there may be patterning and etching of these final layers. For example, they may have exposed features where the encapsulated battery may be electrically contacted. Some examples will include enclosure in packaging to prevent ingress of one or more of: oxygen, moisture, other gasses and liquids. These examples may therefore include packaging in one or more layers which may include one or more of an insulating layer, which as a non-limiting example may include parylene, and an impermeable layer, which may include for example metals, aluminum, titanium, and similar materials which form an impermeable film layer that may be biocompatible. The impermeable material may include a precision formed/cut cover layer of glass, alumina, silicon, or another material.

Some substrates may be formed from material which provides electrical insulation and alternately some substrates may be electrically conductive or semi-conductive. These alternate aspects of the substrate material, nonetheless, may be consistent with a final thin film battery that may form a thin component which may be integrated into a stacked integrated component device and provide at least in part the energization function of the device.

In examples that comprise a thin film battery where the thin film battery is a thin component of a stacked integrated device, the battery may have connection to the other thin components through access with opening in the passivation films. The connection may be to the outside of the package and may be made in a wireless manner. The connection may be made for example, through a manner including radio frequency connection, capacitive electrical communication, magnetic coupling, optical coupling, or another of the numerous means that define manners of wireless communication.

Portion 420 or any portion in the volume opportunity, may have stored therein and delivered therefrom an active drug. Where an active drug is desired, the ophthalmic device may comprise a reservoir within the body, and the reservoir may comprise an active agent drug containing material. The material may be any material that is compatible with the active drug or reagents to be delivered by the plug and is capable of releasing the active drug in numerous manners. For example, by dissolving or degrading of the material or diffusion of the active drug from the material. Any number of material including, without limitation, polymeric materials including, without limitation, polymeric materials, both naturally occurring and synthetic, non-polymeric materials including, inorganic materials including, without limitation, porous ceramics, lipids, waxes and the lack and combinations thereof.

Preferably, the active agent containing-material is a polymeric material, in which at least one active agent is disposed on, dispersed throughout, or otherwise contained. The body is preferably impermeable to the active agent, and the reservoir has at least one opening through which the active agent may be released.

Depending upon the active agent containing material selected, the active agent may be released from the material almost immediately, or the active agent may be released in a sustained manner over a desired period of time. For example, a polymeric material may be used that is composed of one or more polymers that are at least partially soluble in water. When such polymeric material is exposed to the aqueous environment of the tear fluid, it will preferably dissolve and release the active agent as it dissolved.

Alternately, the active agent may be dispensed with the use of an incorporated microfluidic pump that is capable of dispensing the active agent through energized channels and onto the ophthalmic environment. For example, the microfluidic pump may comprise channels that may be energized to change the contact angle of a solution thereby causing the active agent to be dispensed.

Examples of active drugs or agents may include for example, anti-infective agents including, without limitation, tobramycin, moxifloxacin, ofloxacin, gatifloxacin, ciprogloxacin, gentamicin, sulfisoxazolone diolamine, sodium sulfacetamide, neomycin propanidine, sulfadiazine and pyrimethamine.

Additionally or alternately, the ophthalmic device may deliver antiviral agents, including without limitation, formivirsen sodium, foscarnet sodium, trifluridine, tetracaine HCL, natamycin and ketocaonazole. Furthermore, analgesics may also be included and may include, for example and without limitation, acetaminophen, and codeine, ibuprofen and tramadol. Finally, some examples may also deliver active drugs or agents that additionally can comprise, for example and without limitation, vitamins, antioxidants and nutraceuticals including vitamins A, D and E, lutein, taurine, glutathione, zeaxanthin, fatty acids and the like.

Referring now to FIG. 5, another exemplary energized ophthalmic lens configuration is depicted. At 501, a microcontroller may be positioned in a pocket designed in the non-optical portion of the ophthalmic device with respect to an optical portion 505 of the ophthalmic device. Said microcontroller 501 may be in connection with a battery comprising a region of cathode 504 in connection with anode 503 to provide embedded energization.

Further at 502, a reservoir that may comprise a type of pumping mechanism or a substrate capable of dissolving as previously discussed may be included in this section of the device 500. At 506, a layer may be used to encapsulate the components, as it may be desired to avoid direct contact with the ophthalmic environment.

Figure 6:
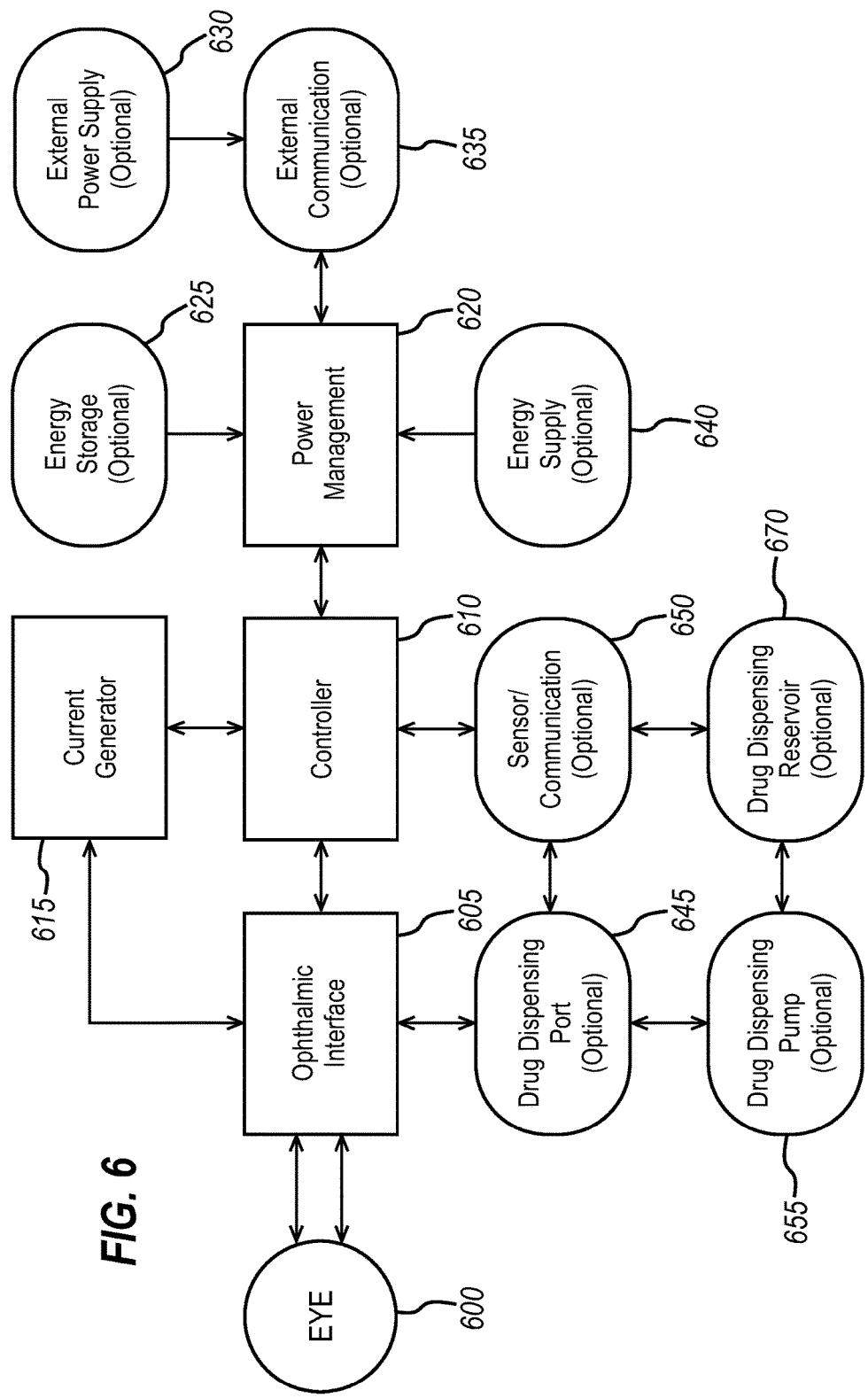
FIG. 6 illustrates a schematic diagram of components that may be included in an aspect of the present invention.

Referring now to FIG. 6, a schematic diagram of exemplary components is depicted. Said components may be embedded into the device using any one or a combination of methods of energizing an ophthalmic device known in the art or novel methods disclosed in other applications by the same inventive entity. For example, using methods to use SIC-Device(s) in optics.

At 600, an eye is in contact or proximate to an ophthalmic interface 605. The ophthalmic interface 605 may include, for example, an exposed contact lens. Said ophthalmic interface 605 may comprise or be in connection with a controller 610, a current generator 615, one or more sensor 650, and a drug dispensing port 645. The controller 610 may be, for example, one as described in FIG. 2, and may further comprise additional microcontroller(s), timers, signal conditioning devices, state machine devices, and/or event triggering devices. The current generator 615 may be capable of generating voltage-mode or current-mode, for example, DC or AC and different Waveforms and frequencies. The sensor 650 may include a sensor used to sense and/or monitor a wound or to provide communication with the device, for example a photo sensor or an antenna.

Where an active agent or drug is desired, the drug dispensing port 645 may be in connection with a drug dispensing reservoir 670 and comprise a pumping means or polymer functional to dissolve and dispense active component as it may be desired 655, for example upon entering the ophthalmic environment or a signal 650.

Additionally, the controller 610 may be in connection with the dispensing port 645, one or more sensors 650, and/or power management device 620. The power management device may include, for example a rectifier, filter, voltage regulator and battery charger, and may be in communication with one or more of a energy storage device 625, external power supply 630 or an internal energy supplier 640. The external energy supply 630 may include, for example solar cell, coil (inductive), antenna (RF), thermoelectric, piezoelectric, "Energy Harvesting", etc. The external power supply communication 635 may be LED, inductive, EF, etc. The communication may occur with a device that may be positioned in proximity with the ophthalmic device, for example glasses or a patch.

Energy storage 625 may be necessary in other examples. Energy storage means may include, for example, a battery (alkaline, Li-Ion, Li, Zn-air, etc.), a capacitor or a super capacitor embedded in the lens using for example SIC-Device technology.

Referring now to FIG. 7, an exemplary electrical system 700 for monitoring and improving the healing of a wound 714 is depicted. A battery 702 or other suitable power source, as previously described, may provide energy to an electronic generator circuit 704. This generator may create a desired voltage and current required to improve healing of wound 714 using one or more of several techniques known in the art. This circuit may regulate down from the battery voltage, for example delivering 0.25 V across the wound from a 4V battery. This may be done through the use of a common linear voltage regulator. It may also be possible to produce a voltage higher than that available from the battery by including, for example using a charge pump to create a 5V potential from a 1.5V battery. The electronic circuit 704 may connect to a switching network 706. This switching network may be realized through, for example, MOSFET switches in an H-bridge. The switching network 706 may be connected to contacts 710 and 712. These contacts may provide electrical connections to the wound allowing current to flow from the wound 714 to the switching network 706. Switching network 706 may also be connected to a sensor circuit 708. Such a sensor may detect the voltage induced across the wound by the healing process. The sensor may also measure parameters of the wound, such as voltage, current, and resistance.

Figure 8:
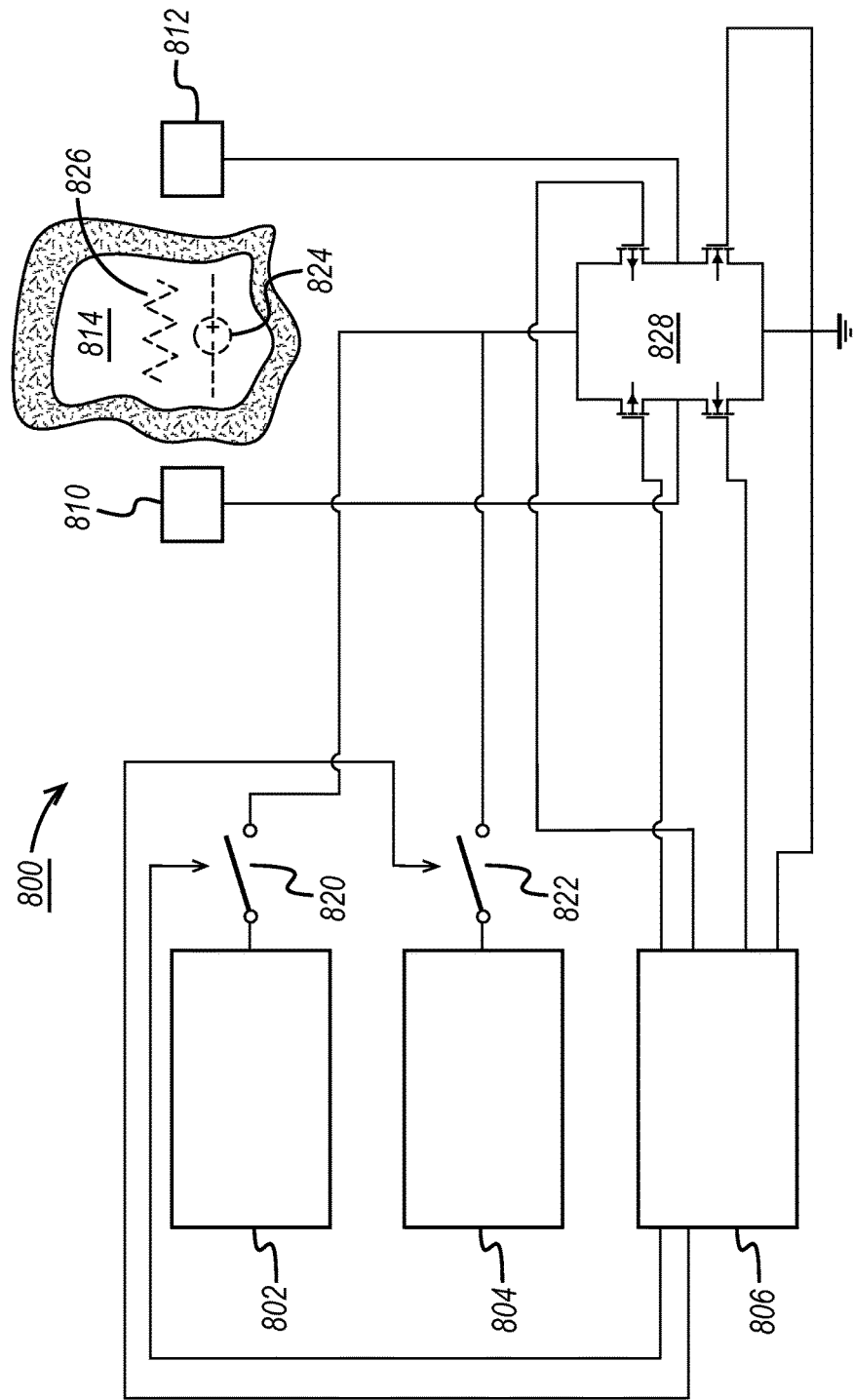
FIG. 8 illustrates a circuit schematic of an electrical system for monitoring and improving the healing of a wound.

Referring now to FIG. 8, a circuit schematic of an electrical system 800 for monitoring and improving the healing of wound 814 is depicted. As previously described, the wound 814 has an associated electric field that may be represented by the voltage source 824. The wound may also have a measurable resistance 826 different than that of the surrounding tissue. Contacts 810 and 812 may be positioned suitably close to the wound, as previously discussed. Also as previously discussed, these contacts may be of appropriate biocompatible, conductive materials or encapsulated by biocompatible conductive materials. Contacts 810 and 812 may connect to a switching network 828, shown as an H-bridge, a common circuit known in the field of electronics, which may permit connecting, disconnecting, and toggling the polarity of applied or measured voltage and current. Controller 806 may control the switching network 828 along with switches 820 and 822. The switches may be implemented with MOSFET devices, as is common in the industry. The controller may be implemented as a microcontroller, for example. Switch 820 may connect to generator block 802 to the switching network 828. This generator block 802 can contain the circuitry necessary to generate the voltage, current, waveforms, and frequencies desired for wound healing Switch 822 may connect sensor block 804 to the switching network 828. The sensor block 804 which may measure voltage 824, resistance 826, or other parameters of wound 814. For example, the measurable field 824 across the wound which may vary with wound healing or infection such that sensor 804 can detect such states and changes to those states.

In one system state, switch 822 may be closed while switch 820 may be open, and the desired switches in switching network 828 may be enabled and disabled to connect the sensor 804 to the wound 814 through contacts 810 and 812 without connecting the generator 802.

Sensor 804 may be designed to measure voltage with techniques common in the electronics industry, for example a differential or instrumentation amplifier. Sensor 804 may also be configured as a capacitance sensor, resistance sensor, or other electrical sensor. In another system state, switch 820 may be closed while switch 822 may be left open. The generator 802, programmed to the desired parameters for wound healing, may connect through switching network 828 and contacts 810 and 812 to wound 814.

Generator 802 may be operated as a controlled voltage source, controlled current source, or an AC generator to promote healing. As previously discussed, voltages in the range of 0.25-0.5V may be desired across wound 1514 to promote healing, although generator 802 may be designed for various voltage, current, and frequency ranges. The states of 802 and 828 may be varied during healing, for example to reverse current to change the direction of cell growth or to pulse between directed and undirected healing Alternatively, or in addition, the generator 802 may contain circuitry which detects voltage or current across or through the wound 814 while the corresponding value of current or voltage is applied to the wound. These parameters may be monitored during healing and the controlled voltage or current modified accordingly. This may replace or supplement sensor 804. Components 802, 804, and 806 are powered from a suitable energy source (not shown) such as a battery or inductive power transfer.

A wide range of applied electric fields and induced have been suggested to promote wound healing, for example 10 millivolts to 5 Volts per millimeter depending on tissue and specified therapy. Likewise, a range of electric fields and currents have been measured across injured tissues. Generators such as 802 and sensors such as 804 should have sufficient range of capabilities (voltage, current) and programmability to supply and measure therapeutic and diagnostic parameters. Alternatively, the circuits may be highly customized for particular therapeutic and diagnostic requirements.

As is described in the background and references, wounds may be detected by passing a sensor over healthy and wounded tissue. Measurements of current density, for example, show clear deviations as probes are passed over wounds as opposed to nearby healthy tissue. A therapeutic system may be designed and manufactured with specific geometry that is compatible with common wounds, for example incisions used during eye surgery in certain preferred locations. A multitude of therapeutic systems may be manufactured to cover a range of wound geometries. 3D printing or other just-in-time, on-site manufacturing techniques may allow physicians to measure wound geometry and manufacture custom therapeutic devices. A therapeutic system may contain several electrical contacts positioned around the tissue. Sensors could detect wound geometry and send therapeutic currents through only the desired contacts.

Referring now to FIG. 9, an exemplary therapeutic system 900 for detecting and improving the healing of wounds across a range of wound locations is depicted. Tissue 902 contains a wound 904. Contacts 906, 908, 910, 912, 914, and 916 may provide electrical contact through biocompatible means as previously discussed. Switching network 918 can allow generator and/or sensor circuitry 920 to connect to certain sensors, for example adjacent pairs. The system may first measure the difference in potential between contacts 906 and 908. The system may then measure 908 and 910, 910 and 912, 912 and 914, and 914 and 916. As explained previously, a measurable difference can exist between contacts 910 and 912, which may be positioned across the wound, from contacts 906 and 908 or 914 and 916. The system may also detect this difference and apply a therapeutic current across only contacts 910 and 912. Another wound, perhaps on another individual, may exist between contacts 906 and 908, for example. The system may detect this wound and apply a therapeutic field to contacts 906 and 908. This concept may be extended with a multi-dimension grid or other arrangement of contacts, to provide for a range of wound lengths, widths, shapes, and locations.

The sensors described herein (e.g., sensor 804) may comprise one or more sensors used to measure resistivity, conductivity, impedance, color relative to surrounding healthy tissue (for example red to correlate with irritation), pH, cytokines, and inflammatory markers. The measurement may be a "global" measurement of the entire wound (cytokines), or may be performed at several points across the wound (resistivity).

The generator described herein (e.g., generator 820) may be a DC supply, either regulated voltage or regulated current. The generator may also be a pulse generator, an AC supply, or an arbitrary waveform generator, for example. The generator may be used, for example, to produce an electrical field in a range of integer values between 1 and 100 mV/mm, and/or a magnetic field (H-field) in a range of integer values from 1 to 10 μA/mm, more specifically an electrical field of about 5, 10, 15, 20, 25, 30, 35, 40, 45, or 50 mV/mm and a magnetic field of 1, 2, 3, 4, 5, 6, 7, 8, 9, 10 μA/mm may be used. Specific examples include producing an electrical field of 25 mV/mm, and/or a magnetic field of 2.2 μA/mm. An example output from the generator is about 65 to 100 MHz at about 10 to 100 V including integer values there between, with a current limited to between about 0.1 and 1.0 mA (e.g., 0.1, 0.2, 0.3, 0.4, 0.5, 0.6, 0.7, 0.8, 0.9 and 1.0 mA). The waveforms may be applied for a period of at least about an hour.

Further example signals output by the generator include one or more of short pulses that are asymmetric and bidirectional, a sinusoidal AC signal, pulsed currents and an extremely short-duration, high-voltage, pulsed, voltage. Typical output values from the generator may include about 100 to 150V (e.g., 100, 105, 110, 115, 120, 125, 130, 135, 140 and 145 V) at 1 to 125 Hz including integer values there between, with a pulse width of 5 to 200 μs (e.g., 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, and 200 μs) and a current of less than about 1.0-2.0 mA (1.0, 1.1, 1.2, 1.3, 1.4, 1.5, 1.6, 1.7, 1.8, 1.9, or 2.0 mA). A further example output waveform includes a twin-peaked, monophasic wave form (i.e., reverse sawtooth) with a current pulse duration of 100 μsec, delivered at a rate of 80 pulses/sec and voltages ranging between about 25 and about 80 V (e.g., 25, 30, 35, 40, 45, 50, 55, 60, 65, 70, 75, 80 V) and including integer values there between. A further example output waveform includes pulses of about 0.1 ms duration at a frequency of about 100 Hz at about 100 V.

The present invention relates generally to an ophthalmic device capable of delivering an electric current to aid in the healing of ocular wounds or erosions. The ophthalmic device may have an embedded energy source or obtain energy through an antenna. The ophthalmic device may also include an active drug contained in a reservoir capable of dispensing the drug upon a condition or a signal and where the reception by the ocular surface of the drug, may be enhanced by said electric field or an additionally emitted electric field.

Various aspects and examples of the present invention are set out in the following non-exhaustive list of numbered clauses:

Clause 1: An apparatus for controlled healing of ocular erosions, the apparatus comprising;

an optical surface comprising an Energizable controller capable of being programmed to transmit energy from an energy source onto/into an ocular surface, through the use of a current generator in electrical connection with energy emitting contacts capable of transmitting an electric field; and wherein the controller, current generator and energy emitting contacts are biocompatible or encapsulated by a conductive biocompatible layer to allow positioning of said apparatus in an ocular surface.

Clause 2: The apparatus of clause 1 wherein the optical surface has an optical power other than about 0.

Clause 3: The apparatus of clause 1 wherein the energy is stored in a battery embedded in the apparatus.

Clause 4: The apparatus of clause 3 wherein the battery is embedded using Stacked Integrated Component Device packaging technologies.

Clause 5: The apparatus of clause 1 wherein the energy of the power source is obtained wirelessly through an RF antenna in connection with said ophthalmic device.

Clause 6: The apparatus of clause 5 wherein the RF antenna is in connection with a device in proximity with the ophthalmic device.

Clause 7: The apparatus of clause 6 wherein the power source device is contained within a pair of glasses.

Clause 8: The apparatus of clause 6 wherein the power source device is contained within a patch.

Clause 9: The apparatus of clause 1 additionally comprising a reservoir capable of containing an active drug to be delivered in a predetermined manner.

Clause 10: The apparatus of clause 1 additionally comprising one or more sensor capable of measuring changes in the naturally emitted electric field by the ocular erosions.

Clause 11: The apparatus of clause 10 additionally capable of delivering an active drug upon the sensor's detection of a change in electric field threshold signaling an infection.

Clause 12: The apparatus of clause 9 wherein the reservoir contains an active drug comprising an analgesic.

Clause 13: The apparatus of clause 9 wherein the reservoir contains an active drug comprising an antiviral agent.

Clause 14: The apparatus of clause 9 wherein the reservoir contains an active drug comprising an anti-infective agent.

The invention claimed is:

1. A contact lens for controlled healing of one or more corneal erosions, the contact lens comprising:
    a biocompatible material configured for placement on a corneal surface;
    a plurality of energy emitting contacts embedded in or on the surface of the biocompatible material;
    an energy source configured to supply energy to the plurality of energy emitting contacts; and
    a controller configured to control the flow of energy to the plurality of energy emitting contacts to create an electrical field across the corneal surface;
    wherein the plurality of energy emitting contacts are configured to surround the one or more corneal erosions; and
    wherein the electric field is created between two or more energy emitting contacts of the plurality of energy emitting contacts.

2. The contact lens of claim 1, wherein the controller is configured to control the flow of energy in order to influence or mediate the directional migration of epithelial cells to promote wound closure or healing.

3. The contact lens of claim 1, wherein the contact lens has an optical power other than 0.

4. The contact lens of claim 1, wherein the energy source is a battery embedded in the contact lens.

5. The contact lens of claim 4, wherein the battery is embedded using stacked integrated component device packaging technologies.

6. The contact lens of claim 1, wherein the energy source obtains energy wirelessly through an RF antenna.

7. The contact lens of claim 6, wherein the RF antenna is in connection with a device in proximity with the contact lens.

8. The contact lens of claim 7, wherein the device is a pair of energized glasses.

9. The contact lens of claim 7, wherein the device is an energized patch.

10. The contact lens of claim 1, additionally comprising a reservoir capable of containing an active drug to be delivered in a predetermined manner.

11. The contact lens of claim 10, additionally comprising one or more sensors capable of measuring a change in the electric field naturally emitted by the corneal erosion.

12. The contact lens of claim 11, wherein said controller is additionally capable of controlling the delivery of the active drug upon the one or more sensors detecting a change in the electric field.

13. The contact lens of claim 12, wherein the active drug comprises an analgesic.

14. The contact lens of claim 12, wherein the active drug comprises an antiviral agent.

15. The contact lens of claim 12, wherein the active drug comprises an anti-infective agent.

16. The contact lens of claim 12, additionally comprising a microfluidic pump capable of dispensing the active drug to the corneal surface.

17. The contact lens of claim 16, additionally comprising a dispensing port in communication with the reservoir, wherein the dispensing port allows dissolution and dispensing of the active drug.

18. The contact lens of claim 1, additionally comprising a switching network capable of connecting applied or measured voltage and current, disconnecting applied or measured voltage and current, and toggling a polarity of applied or measured voltage and current.

19. The contact lens of claim 1, additionally comprising one or more sensors capable of measuring parameters of the corneal erosion and surrounding healthy tissue, wherein the parameters include at least one of a conductivity, an impedance, a color, a pH, the presence of a cytokine and the presence of an inflammatory marker.

20. The contact lens of claim 19, wherein the one or more sensors measure the change in a naturally emitted electric field of the corneal erosion through the energy emitting contacts.

* * * * *